(12) United States Patent
Luo et al.

(10) Patent No.: US 10,215,667 B1
(45) Date of Patent: Feb. 26, 2019

(54) SAMPLING AND PREPARATION SYSTEM AND ITS IMPLEMENTATION METHOD

(71) Applicant: Zhejiang University, Hangzhou, Zhejiang Province (CN)

(72) Inventors: Zhongyang Luo, Hangzhou (CN); Yuxing Tang, Hangzhou (CN); Chunjiang Yu, Hangzhou (CN); Mengxiang Fang, Hangzhou (CN); Qinhui Wang, Hangzhou (CN); Tao Wang, Hangzhou (CN)

(73) Assignee: Zhejiang University, Hangzhou, Zhejiang Province (CN)

(*) Notice: Subject to any disclaimer, the term of this patent is extended or adjusted under 35 U.S.C. 154(b) by 0 days.

(21) Appl. No.: 15/858,548

(22) Filed: Dec. 29, 2017

(30) Foreign Application Priority Data

Nov. 20, 2017 (CN) .......................... 2017 1 1154527

(51) Int. Cl.
| | |
|---|---|
| *G01T 1/20* | (2006.01) |
| *G01N 1/22* | (2006.01) |
| *B01D 53/50* | (2006.01) |
| *B01D 53/34* | (2006.01) |
| *G01T 1/204* | (2006.01) |
| *G01N 33/00* | (2006.01) |

(52) U.S. Cl.
CPC ......... *G01N 1/2205* (2013.01); *B01D 53/346* (2013.01); *B01D 53/50* (2013.01); *G01N 1/2258* (2013.01); *G01N 33/004* (2013.01); *G01T 1/204* (2013.01); *B01D 2258/0283* (2013.01); *F23C 2900/01001* (2013.01); *G01N 2033/0093* (2013.01)

(58) Field of Classification Search
CPC ............. G01N 31/005; G01N 33/0013; G01N 33/0032
See application file for complete search history.

(56) References Cited

U.S. PATENT DOCUMENTS

| | | | | |
|---|---|---|---|---|
| 4,019,864 A | * | 4/1977 | Saito .................... | G01N 31/005 250/303 |
| 4,368,008 A | * | 1/1983 | Budzich ................. | F01L 25/06 417/267 |
| 5,279,970 A | * | 1/1994 | Patashnick ......... | G01N 15/0618 110/217 |

FOREIGN PATENT DOCUMENTS

JP          2005291539 A    * 10/2005

* cited by examiner

*Primary Examiner* — Kiho Kim
(74) *Attorney, Agent, or Firm* — David D. Brush; Westman, Champlin & Koehler, P.A.

(57) ABSTRACT

A sampling and preparation system is positioned in a coal and biomass co-fired power station, which includes a sampling pipe connected with a boiler flue of the co-fired power station. The sampling pipe from the end close to the boiler flue to the other end away from the boiler flue includes a filtering device, a mass flow controller, a carbon dioxide trap and a pumping device. The sampling and preparation system also includes a carbon dioxide transfer device and a $^{14}C$ testing device. The carbon dioxide transfer device is applied to transferring the carbon dioxide from the carbon dioxide trap to the $^{14}C$ testing device which is applied to measuring the $^{14}C$ in the carbon dioxide sample. The system may calculate the biomass blending ratio of the coal and biomass co-fired power station rapidly.

9 Claims, 13 Drawing Sheets

SAMPLING AND PREPARATION SYSTEM AND ITS IMPLEMENTATION METHOD

CROSS-REFERENCE TO RELATED APPLICATIONS

The present application is based on, and claims priority from, Chinese Patent Application No. 201711154527.X, filed on Nov. 20, 2017, entitled "A sampling and preparation system and its implementation method", the disclosure of which is hereby incorporated by reference herein in its entirety.

TECHNICAL FIELD

The present invention involves the field of isotope detection, in which a sampling and preparation system and its implementation method are disclosed.

BACKGROUND ART

At present, coal is still the main fuel in the power industry. With the social development and economic improvement, there is a sharp increase of demand of electric power, and a sharp decrease of coal storage, and also huge damage to our environment.

However, biomass is a renewable energy containing carbon. It is the characteristics of carbon neutral make biomass energy be applied for replacing part of fossil energy represented by coal, and reducing emission of carbon dioxide to mitigate greenhouse effect.

Biomass and coal co-fired is an excellent method for biomass energy large-scale utilization. It is an efficient and environmental method for producing energy, which can not only decrease the emission of pollution and carbon dioxide, but also utilize the biomass fuel with low heat value efficiently.

Radiocarbon ($^{14}C$) is a radioactive isotope of carbon, which was first discovered by Martin Kamen and Sam Ruben at the Radiation Laboratory of UC Berkeley in Feb. 27, 1940.

The cosmic rays hitting nitrogen atoms in the atmosphere make the $^{14}C$ production. The living creatures' $^{14}C$ radioactivity is consistent with the atmosphere level, because of the atmosphere carbon cycle. However, the coal's $^{14}C$ radioactivity decays mostly, because of being buried deep in the ground for millions of years. So, the power station burn the biomass or not, and how much their burned, in other words, how is the blending ratio could be known by sampling the flue gas in the boiler flue of coal and biomass co-fired power station and measuring the $^{14}C$ in the carbon dioxide.

The biomass blending rate detection technology, this invention involves, is based on the radiometric dating of $^{14}C$ isotopes. This technique was first applied for research of archaeology and geology. Nowadays, it is also applied for identification of biological base materials and detection of bio fuel rate in the garbage incineration power station as an effective method for biological component identification.

Differ from the situation of garbage incineration power station, the supply of bio fuel is affected by season, which make the biomass blending rate is no more than 5% in the coal and biomass co-fired power station. While the biomass blending rate is low, accelerator mass spectrometry (AMS) is the most accurate detection method for $^{14}C$ radioactivity, but the equipment is too expensive to be popularized.

Lacking of effective and reliable detection technology and device of biomass blending rate make it unable that the government formulate standards and policies for coal and biomass co-fired power generation subsidies, which limits the development of co-fired power generation technology and its market development.

SUMMARY OF THE INVENTION

The exemplary embodiments of the present invention provide a sampling and preparation system and method, for calculating the biomass blending ratio in a coal and biomass co-fired power station rapidly.

An exemplary embodiment of the present invention provides a sampling and preparation system, set in a coal and biomass co-fired power station, including:

a sampling pipe connects with a boiler flue of a co-fired power station, and the sampling pipe from the end close to the boiler flue to the other end away from the boiler flue are sequentially arranged as:

a filtering device, a mass flow controller, a carbon dioxide trap and a pumping device;

the sampling and preparation system further includes a carbon dioxide transferring device and a $^{14}C$ testing device, the carbon dioxide transferring device is used to transferring the carbon dioxide from the carbon dioxide trap into the $^{14}C$ testing device, and the $^{14}C$ testing device is used for measuring the $^{14}C$ in the carbon dioxide.

An exemplary embodiment of the present invention provides a sampling and preparation method used for measuring the $^{14}C$ in a boiler flue of a coal and biomass co-fired power station, which includes the following steps:

Filtering and fixing step: filtering the particulate matter and water in the flue gas, and fixing the carbon dioxide of the pure flue gas in a carbon dioxide trap.

Flue gas measuring step: obtaining the amount of the pure flue gas entering the carbon dioxide trap by a mass flow controller.

Transferring step: transferring the carbon dioxide from the carbon dioxide trap into the $^{14}C$ testing device.

$^{14}C$ testing step: measuring the $^{14}C$ of the carbon dioxide in a $^{14}C$ testing device.

Compared to the prior art, the exemplary embodiments of the present invention obtain accurate filtered flue gas measurement by using the mass flow controller after sampling directly by using the sampling pipe in a boiler flue. By using the carbon dioxide transfer device and the $^{14}C$ testing device, the biomass blending ratio measurement of coal and biomass co-fired power station may be completed well without excessive manual intervention.

The present invention has the advantages of accurate result, low cost and short time needed.

Preferably, the carbon dioxide trap includes:

a capturing vessel for fixing the carbon dioxide, and a temperature adjusting device for adjusting the temperature of the capturing vessel.

An evacuation valve is positioned in the part between the pumping device and the carbon dioxide trap on the sampling pipe. And the preposition valve is positioned in the part between the mass flow controller and the carbon dioxide trap on the sampling pipe.

The transferring device includes a transferring pipe line, one end of the transferring pipe line is connected with the carbon dioxide trap and the other end of the transferring pipe line is connected with the $^{14}C$ testing device.

A first transferring valve is positioned on the transferring pipeline.

The temperature adjusting device set in the carbon dioxide trap may warm the carbon dioxide fixed in the carbon dioxide trap slowly. By controlling the pressure and temperature of the capturing vessel, it may gain the liquid carbon dioxide directly in the carbon dioxide trap. Then it is possible to transfer the liquid carbon dioxide into the $^{14}C$ testing device conveniently through the first transferring valve to be tested.

Preferably, the transferring pipeline from the end close to the carbon dioxide trap to the other end away from the carbon dioxide trap is sequentially arranged as:

a gas compressor, a pressuring vessel, a second transferring valve and a transferring pump.

The first transferring valve is positioned between the gas compressor and the carbon dioxide trap.

The gas compressor is used to compress the carbon dioxide to liquid or supercritical state in the pressuring vessel.

The transferring pump is used to transfer the carbon dioxide from the pressuring vessel into the $^{14}C$ testing device.

Preferably, in the transferring step, the following sub-step is also included:

the carbon dioxide is pretreated to liquid or supercritical state.

It is better to control the carbon dioxide in the pressuring vessel by using the gas compressor, and is easier to gain the liquid or supercritical carbon dioxide. Then the measuring accuracy might be improved.

Preferably, the transferring device also includes a vacuum pump, the vacuum pump is connected with the transferring pipeline by the pipeline branch, and a vacuum valve is positioned on the pipeline branch.

The vacuum pump pumps the system to vacuum, avoids the effect of original gas to the gas pressure and improves the testing accuracy.

Preferably, the sampling and preparation system also includes: a heat exchange pipeline connected to the outlet of the pumping device. The heat exchange pipeline is used to exchange the heat with the part on sampling pipe between the boiler flue and the filtering device.

The heat exchange pipeline may decrease the temperature of the flue gas entering the sampling and preparation system, and decrease the cooling requirement of the carbon dioxide trap. It saves the system energy consumption, decreases the time required to fix carbon dioxide in the carbon dioxide trap and improves the efficiency of sampling and preparation.

Preferably, the filtering device comprises the following sequentially connected units:

a preposition dust filter, a dryer and a postposition dust filter.

There is a cold trap positioned between the mass flow controller and the carbon dioxide trap, and the temperature of the cold trap ranges from minus 40 degrees Celsius to minus 60 degrees Celsius.

Preferably, between the gas testing step and the transferring step, it is also includes the following step:

the secondary filtering step: passing the flue gas through the cold trap to remove the sulfur oxides and nitrogen oxides in the flue gas.

The purity of carbon dioxide is improved by using the filtering device to filter the impurity in the flue gas and by using the cold trap to purify and fix the carbon dioxide and then the detection accuracy is improved. The liquid scintillation counter is used in the exemplary embodiments of the present invention, and the cost of the instrument automation is reduced. It will improve the competition of the liquid scintillation counter in the application of biomass bending ratio detection.

Preferably, the $^{14}C$ testing device includes an optical fiber, a scintillation counter and a $^{14}C$ testing bottle.

The $^{14}C$ testing bottle includes a pressure-bearing shell and the sample bin positioned in the pressure-bearing shell, a cavity is arranged in the sample bin and the $^{14}C$ testing bottle is provided with an injection port connected to the cavity;

the injection port is connected with the transferring device; the sample bin diffuses the light produced in the cavity; a scintillator is pre-set in the cavity.

At least part of the sample bin is transparent. An optical fiber channel is set on the pressure-bearing shell, one end of the optical fiber channel is connected with the scintillation counter and the other end of the optical fiber channel is connected with the transparent part of the sample bin.

An insulation layer is positioned between the pressure-bearing shell and the simple bin.

A sensory assembly is positioned in the cavity.

The cavity is spherical or cylindrical.

One end of the optical fibers is inserted into the optical fiber channel, and the other end is connected to the scintillation counter.

The sensory assembly is pressure sensor and/or temperature sensor.

Preferably, the following sub-step is also included in the $^{14}C$ testing step: mixing step: mixing up liquid carbon dioxide or supercritical carbon dioxide and a scintillator, then setting it in a dark condition for a preset standing time;

counting step: counting the mixture by using a scintillation counter.

If the carbon dioxide is pretreated into liquid state, the mixing ratio of liquid carbon dioxide and scintillator is from 10:1 to 100:1 (volume ratio) during the mixing step.

If the carbon dioxide is pretreated into supercritical state, the mixing ratio of the supercritical carbon dioxide and the scintillator is from 0.16 L/g to 0.4 L/g (volume mass ratio).

By setting a pressure-bearing shell outside the sample bin, the carbon dioxide in the cavity of the sample bin may be kept in a relatively stable phase state, so that the carbon dioxide may be fully mixed with the scintillator. By setting the cavity which diffuses reflection, the high-energy electrons decay from the $^{14}C$ in the carbon dioxide may collide with scintillator monomer, so that the scintillator monomer is in the excited state. When the scintillator monomer is de-excitation, a photon with a wavelength of about 380 nm will be generated. These photons may enter the external scintillation counter through the optical fiber channel, so that the $^{14}C$ in the carbon dioxide sample may be measured. The $^{14}C$ testing bottle has the advantages of simple structure, low cost, accurate test and short time needed. The $^{14}C$ testing method of the exemplary embodiments of the present invention, mixing the liquid or supercritical carbon dioxide with the scintillator directly and standing it, compared with converting carbon dioxide into benzene, makes chemical reactions of carbon dioxide unnecessary takes shorter testing time and measures more accurate.

In the figures:
1 $^{14}C$ testing device:
11 $^{14}C$ testing bottle;
111 pressure-bearing shell; 112 simple bin; 1121 body of sample bin; 1122 transparent sheets; 1123 seal ring; 113 cavity; 114 optical fiber channels; 115 insulation layer; 116 air holes; 117 sensory assembly;
12 optical fiber; 13 scintillation counter;
2 filtering device; 21 preposition filter; 22 dryer; 23 postposition filter;
3 mass flow controller;
4 carbon dioxide trap;
5 pumping device;
6 boiler flue;
7 sampling pipe; 71 evacuation valve; 72 prepositioned valve; 73 heat exchange pipeline
8 carbon dioxide transferring device: 81 transferring pipeline; 82 first transferring valve; 83 gas compressor; 84 pressure vessel; 85 second transferring valve; 86 transferring pump; 87 vacuum pump; 88 pipeline branch; 89 vacuum valve;
9 cold trap.

DETAILED DESCRIPTION OF THE ILLUSTRATIVE EMBODIMENT

First Embodiment

Figure 1:
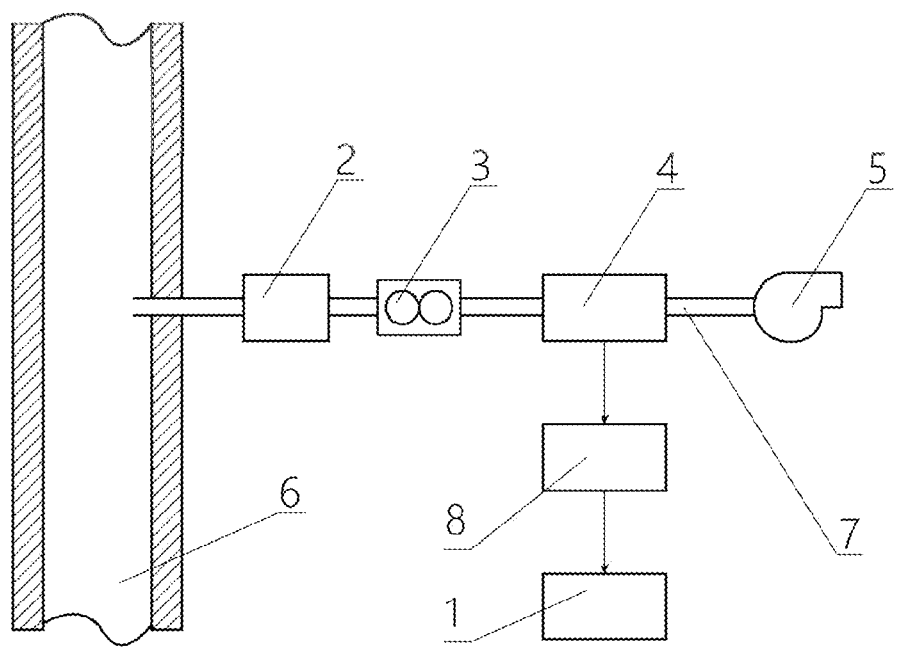
FIG. 1 is a connection diagram of the sampling and preparation system in the first embodiment.

The first embodiment provides a sampling and preparation system, set in a coal and biomass co-fired power station, as shown in the FIG. 1, including:

The sampling pipe 7 connected with the boiler flue 6 of the co-fired power station, and the sampling pipe 7 from the end close to the boiler flue 6 to the end away from boiler flue 6 are sequentially arranged as: the filtering device 2, the mass flow controller 3, the carbon dioxide trap 4 and the pumping device 5.

The sampling and preparation system also includes the carbon dioxide transferring device 8 and the $^{14}C$ testing device 1. The carbon dioxide transferring device 8 is used to transferring the carbon dioxide from the carbon dioxide traps 4 into the $^{14}C$ testing device 1, and the $^{14}C$ testing device 1 is used for measuring the $^{14}C$ in the carbon dioxide.

The arrow in the FIG. 1 presents the transferring direction of the carbon dioxide.

The carbon dioxide trap 4 in the present embodiment may be a cryogenic trap container, in particular, a cryogenic vessel with temperature less than or equal to −78.4 degrees centigrade. Carbon dioxide condenses in the carbon dioxide trap 4 as solid state, then which can be transferred into the $^{14}C$ testing device 1 by heating, sublimation, etc.

The $^{14}C$ testing device 1 maybe a variety of test devices. As the recommendation of the present embodiment, it is usually to choose the testing device related with liquid scintillation counting principle.

Figure 2:
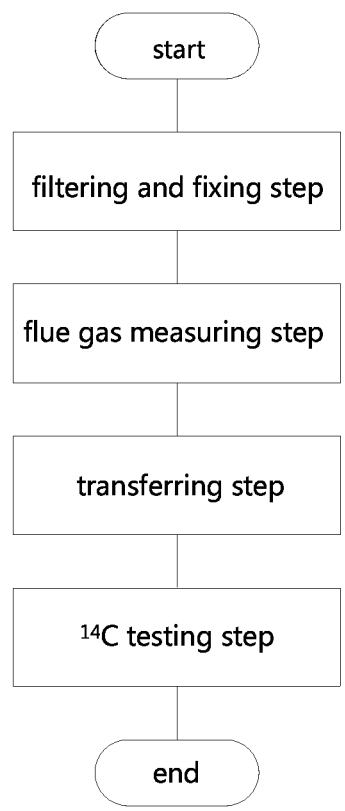
FIG. 2 is a flow chat of the sampling and preparation method according to the first embodiment.

The first embodiment also provides a sampling and preparation method used for measuring the $^{14}C$ in the boiler flue 6 of the coal and biomass co-fired power station, as shown in the FIG. 2, includes the following steps:

filtering and fixing step: filtering the particulate matter and water in the flue gas, and fixing the carbon dioxide of the pure flue gas in the carbon dioxide trap 4;

flue gas measuring step: obtaining the amount of the pure flue gas entering the carbon dioxide trap 4 by the mass flow controller 3;

transferring step: transferring the carbon dioxide from the carbon dioxide trap 4 into the $^{14}C$ testing device;

$^{14}C$ testing step: measuring the $^{14}C$ of the carbon dioxide in the $^{14}C$ testing device 1.

Moreover, it is preferably to include blending ratio calculating step: calculating the blending ratio of the coal and biomass co-fired power station by using the obtained measurement of $^{14}C$ and the flue gas amount.

The biomass blending ratio may be calculated by the following formula.

$$c_{flue\ gas,B} = \frac{A_{sample}}{A_{ON}} \times 100\%$$

$$A_{ON} = \frac{0.95 A_{ox1N}}{\left(1 - 2 \cdot \frac{19 - 25}{1000}\right)} \times C_{anthro} \times 100\%$$

$$\text{Blending ratio}_{mass} = m_B / m_{Coal} = \frac{c_{flue\ gas,B}}{c_{C,B}} \bigg/ \frac{1 - c_{flue\ gas,B}}{c_{C,Coal}}$$

$$\text{Blending ratio}_{energy} = \frac{H_B}{H_{Coal}} = \frac{m_B \cdot Q_{Low,B}}{m_{Coal} \cdot Q_{Low,Coal}}$$

The meaning of each parameter in the above formula is as follows:

$c_{flue\ gas,B}$—The ratio of carbon dioxide produced by biomass combustion to total carbon dioxide in flue gas [Vol-%];

$A_{sample}$—Activity of $^{14}C$ in the sample under test [DPM/gC], the unit means the number of flashes measured per minute in carbon per gram;

$A_{ON}$—The general activity of $^{14}C$ in biomass today [DPM/gC];

$A_{ox1N}$—Activity of $^{14}C$ in the NBS SRM 4990b standard materials, [DPM/gC], its coefficient is 0.95 times because of "after 1950, a number of standards were developed, and we commonly use" absolute international standard activity (AISA)", which is defined as 95% of $^{14}C$ content in the NBS SRM 4990b standard material". The divisor is due to that, the $^{13}C$ value of oxalic acid in the AISA is −19‰, however, the $^{13}C$ value of the biomass (wood) is generally considered to be −25‰, and there is a certain numerical relationship between the value of the $\delta^{14}C$ and the value of $\delta^{13}C$ in the material."; $C_{anthro}$—The correction factor, for human activities which causes dramatic changes of $^{14}C$ concentration in atmospheric, for example:

Suess effect (diluting year by year) and nuclear test (inflating in short time);
Blending ratio$_{mass}$—Biomass blending ratio, mass basis[kg/kg];
Blending ratio$_{energy}$—Biomass blending ratio, energy basis [MJ/MJ];
$m_B$—Mass ratio of biomass in total fuel [kg/kg];
$m_{Coal}$—Mass ratio of coal in total fuel [kg/kg];
$c_{C,B}$—Mass content of carbon in biomass [kg/kg];
$c_{C,Coal}$—Mass content of carbon in coal[kg/kg];
$H_B$—Energy ratio of biomass in total energy supply [MJ/MJ];
$H_{Coal}$—Energy ratio of coal in total energy supply [MJ/MJ];
$Q_{Low,B}$—Low calorific value of biomass [kJ/kg];
$Q_{Low,Coal}$—Low calorific value of coal[kJ/kg].

The sampling and preparation system present in the present invention realizes the measurement of biomass blending ratio in the coal and biomass co-fired power station, which has the advantages of accurate measurement results, low cost and short testing time. Liquid scintillation counter is used in on the embodiment, and the cost of the instrument automation realizing may be reduced, which will improve the competition of the liquid scintillation counter in the application of biomass bending ratio detection.

Compared to the prior art, the exemplary embodiments of the present invention obtain accurate filtered flue gas measurement by using the mass flow controller 3 after sampling directly by using the sampling pipe 7 in a boiler flue 6. By using the carbon dioxide transfer device 8 and the $^{14}C$ testing device 1, the biomass blending ratio measurement of coal and biomass co-fired power station may be completed well without excessive manual intervention.

The present invention has the advantages of accurate result, low cost and short time needed.

Second Embodiment

The second embodiment provides a sampling and preparation system, which is improves the sampling and preparation system in the first embodiment. The main improvement is that, in the second embodiment, as shown in the FIG. 3, the carbon dioxide trap includes:

the capturing vessel 41 for fixing the carbon dioxide, and the temperature adjusting device 42 for adjusting the temperature of the capturing vessel 41.

The evacuation valve 71 is positioned on the sampling pipe 7, between the pumping device 5 and the carbon dioxide trap 4. And the preposition valve 72 is positioned on the sampling pipe 7, between the mass flow controller 3 and the carbon dioxide trap 4.

The transferring device includes the transferring pipeline 81, one end of the transferring pipeline 81 is connected with the carbon dioxide trap 4 and the other end of the transferring pipeline 81 is connected with the $^{14}C$ testing device 1.

The first transferring valve 82 is positioned on the transferring pipeline 81.

Figure 4:
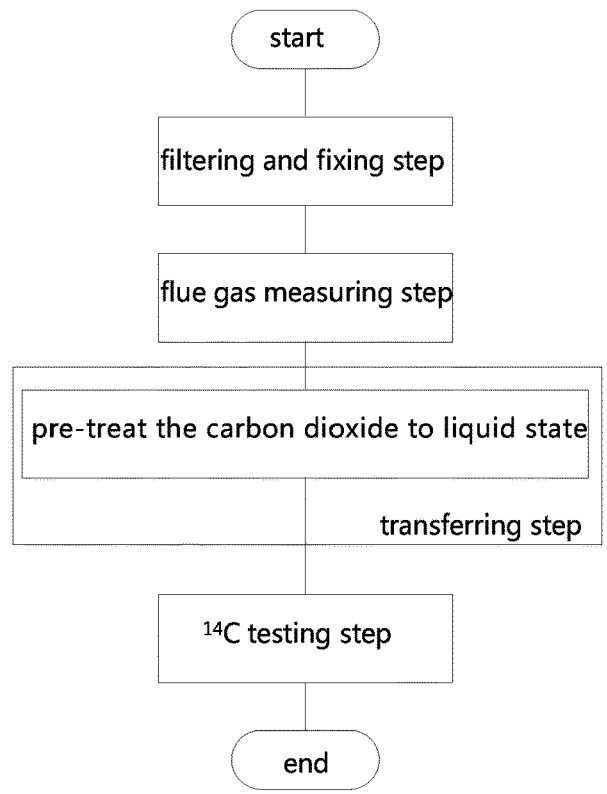
FIG. 4 is a flow chat of the sampling and preparation method according to the second embodiment.

The present embodiment also provides a kind of sampling and preparation method, which further improves the sampling and preparation method in the first embodiment. The main improvement is that, in the second improvement, as shown in the FIG. 4, in the transferring step, the following sub-step is also included: pre-treat the carbon dioxide to liquid state.

Preferably, in the present embodiment, it is better to include the following step.

1. The first transferring valve 82 is closed, while the prepositioned valve 72 and the evacuation valve 71 is opened. The carbon dioxide passing though the carbon dioxide trap 4 is condensed constantly under the effect of a low temperature, and forms solid carbon dioxide in the capturing vessel 41.

2. When enough carbon dioxide is captured in the carbon dioxide trap 4, closing the preposition valve 72 and the evacuation valve 71. The solid carbon dioxide in the capturing vessel 41 is warmed slowly by the temperature adjusting device 42. By controlling the temperature and pressure of the capturing vessel 41 at the same time, the carbon dioxide is converted to liquid state.

3. Opening the first transferring valve 82, the liquefied carbon dioxide flows into the $^{14}C$ test device 1.

Figure 3:
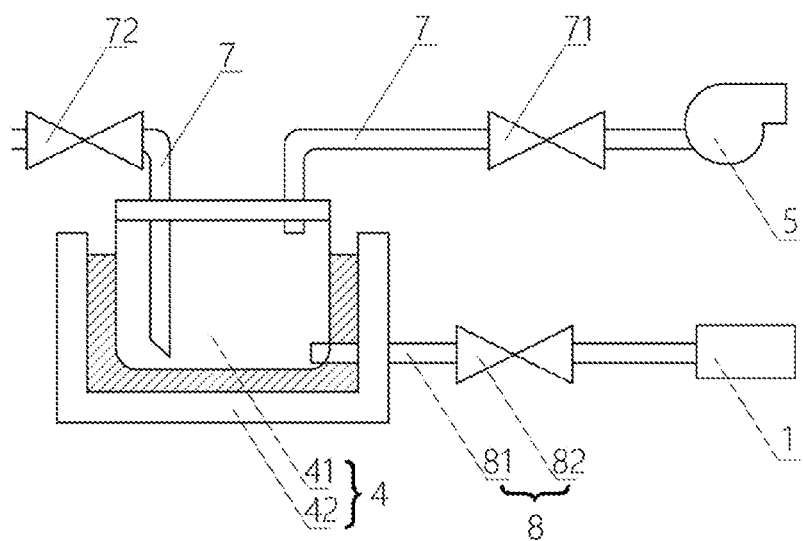
FIG. 3 is a connection diagram of the sampling and preparation system's carbon dioxide trap, carbon dioxide transferring device, pumping device and the $^{14}C$ testing device according to the second embodiment.

The transferring pipeline 81 may be as shown in the FIG. 3, set and connected to the bottom of the capturing vessel 41. Such a connection method is more suitable for the present embodiment which gains liquid carbon dioxide directly in carbon dioxide trap 4.

It is worth mentioning that, the above steps are only one sample preparation procedure suitable for the structure of the present embodiment. In the actual sample preparation process, a variety of adjustments may be made according to the requirements, including but not limited to the following adjustment methods:

the pump is positioned on the sampling pipe 7. It pumps the liquid carbon dioxide into the $^{14}C$ testing device 1 improves the efficiency and reduces the temperature loss.

The buffer bottle is positioned on the sampling pipe 7, using the same principle, liquid carbon dioxide is generated in the buffer bottle, instead of be formed directly in the carbon dioxide trap 4.

The temperature sensor, pressure sensor and other sensors are positioned in the capturing vessel 41, which are connected to the control module of the evacuation valve 71 to adjust its opening, and then the temperature and pressure in the capturing vessel 41 is adjusted to form the liquid carbon dioxide conveniently.

Compared to the prior art, the invention may make the liquid carbon dioxide enter the $^{14}C$ testing device 1 passing through the first transferring valve 82 conveniently, then testing and measuring. It reduces the manual intervention, improves the measuring efficiency, and decreases the cost.

Third Embodiment

Figure 5:
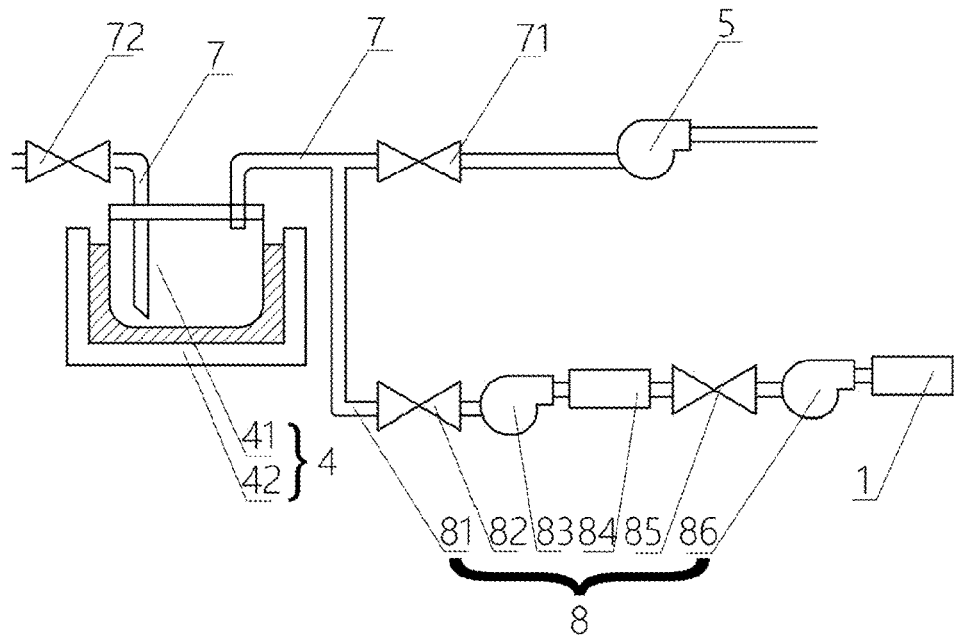
FIG. 5 is a connection diagram of the sampling and preparation system's carbon dioxide trap, carbon dioxide transferring device, pumping device and the $^{14}C$ testing device according to the third embodiment.

The third embodiment provides a sampling and preparation system, which further improves the sampling and preparation system in the second embodiment. The main improvement is that, in the third embodiment, as shown in the FIG. 5, the transferring pipeline 81 from the end close to the carbon dioxide trap 4 to the end away from the carbon dioxide trap 4 are sequentially arranged as:

the gas compressor 83, the pressuring vessel 84, the second transferring valve 85 and the transferring pump 86.

The first transferring valve 82 is positioned between the gas compressor 83 and the carbon dioxide trap 4.

The gas compressor 83 is used to compress the carbon dioxide to liquid or supercritical state in the pressuring vessel 84.

The transferring pump 86 is used to transfer the carbon dioxide from the pressuring vessel 84 into the $^{14}C$ testing device 1.

Figure 6:
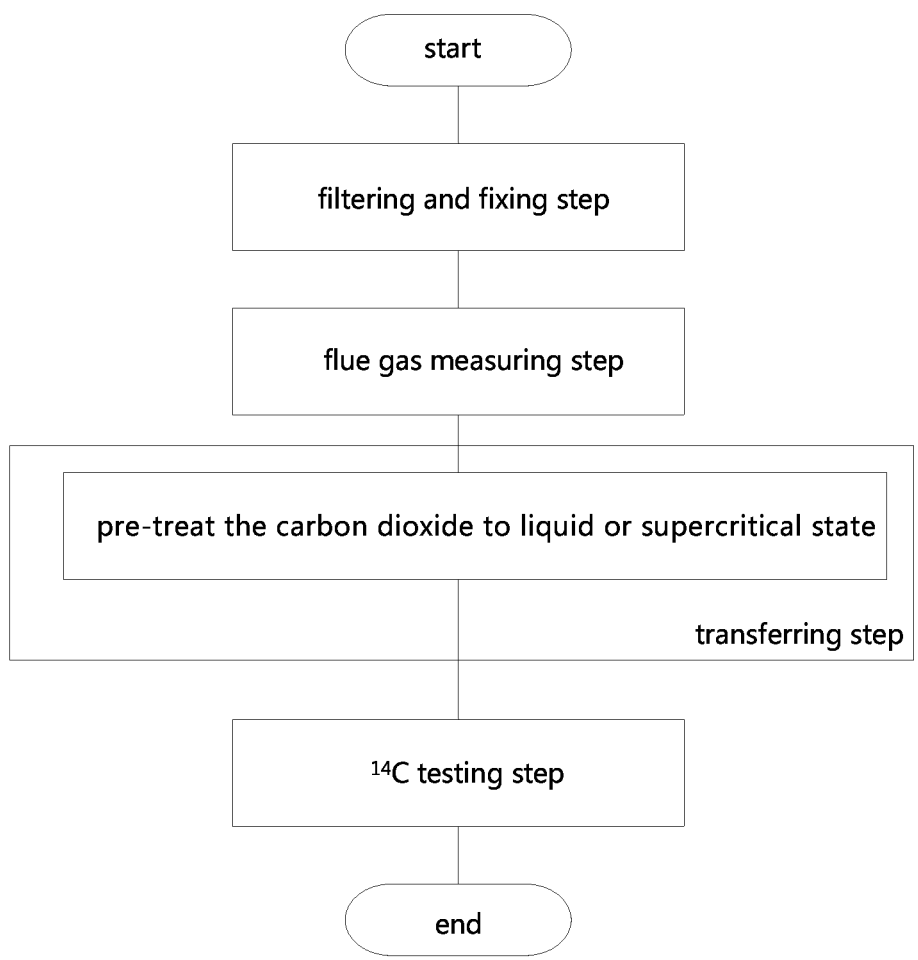
FIG. 6 is a flow chat of the sampling and preparation method according to the third embodiment.

The present embodiment also provides a sampling and preparation method, which is different from the second embodiment, the main difference is that, in the second embodiment, during the transferring step, the carbon dioxide is pretreated to liquid state. However, in the present embodiment, as shown in the FIG. 6, the carbon dioxide is pretreated to liquid state or supercritical state.

In the present embodiment, the transferring pipeline 81 may connect to the capturing vessel 41 directly, or connect to the sampling pipe 7, the part of which between the capturing vessel 41 and the evacuation valve 71.

Preferably, the sampling and preparation system in the present embodiment includes the following steps.

1. The first transferring valve 82 is closed, while the prepositioned valve 72 and the evacuation valve 71 is opened. The carbon dioxide passing though the carbon dioxide trap 4 is condensed constantly under the effect of a low temperature, and forms solid carbon dioxide in the capturing vessel 41.

2. When enough carbon dioxide is captured in the carbon dioxide trap 4, closing the preposition valve 72, the evacuation valve 71 and the second transferring valve 85, and opening the first transferring valve 82 and the gas compressor 83. The solid carbon dioxide in the capturing vessel 41 is warmed slowly by the temperature adjusting device 42, and the carbon dioxide is sublimated to gas state.

3. The carbon dioxide gas is compressed under the action of the gas compressor 83. By controlling the pressure and temperature of the pressuring vessel 84, the liquid carbon dioxide or supercritical carbon dioxide is formed in the pressuring vessel 84. Specifically, when the carbon dioxide is required to form liquid state, the temperature of the carbon dioxide trap 4 may be warm to 0 degree Celsius to 10 degree Celsius slowly and the pressure in the pressuring vessel 84 maybe controlled ranged from 2 MPa to 4 MPa. When the carbon dioxide is required to form supercritical state, the temperature of the carbon dioxide trap 4 may be warm to 30 degree Celsius to 40 degree Celsius slowly and the pressure in the pressuring vessel 84 may be controlled ranged from 7 MPa to 9 MPa.

4. After enough liquid or supercritical carbon dioxide has been gained, closing the first transferring valve 82, and opening the second transferring valve 85 and the transferring pump 86, the carbon dioxide is transferred into the $^{14}C$ testing device 1 by the transferring pump 86. Considering the carbon dioxide residue in the transferring pipeline 81, the content of the carbon dioxide stored in the pressuring vessel may be 1.2 to 2.0 times of one standard testing required, preferably 1.4 to 1.8 times.

In order to control the pressure and temperature in the pressuring vessel 84, as the further optimization of the present embodiment, it is also possible to set pressure sensor and temperature sensor in the pressuring vessel 84.

In the second embodiment, the carbon dioxide can only be treated as liquid, the main reason is that high pressure is necessary in the vessel to arrive the supercritical state. However, it is hard to realize only depending on the carbon dioxide trap 4. In the present embodiment, by setting the gas compressor 83, the carbon dioxide pressure in the pressuring vessel 84 may be better controlled, so it is easier to gain the liquid or supercritical carbon dioxide.

The Supercritical fluid (SCF) is a state of matter, when the temperature and pressure of the matter is beyond the critical value, the properties of gas and liquid tend to be similar, and finally the fluid phenomenon of homogeneous phase will be reached. The supercritical fluid has not only the compressibility like gas, which may effuse like gas, but also the fluidity like liquid. Generally, the density of supercritical fluid is ranged from 0.1 to 1.0 g/ml.

Compared to pre-treating the carbon dioxide to liquid state, pre-treating the carbon dioxide to supercritical state has the advantage of forming the uniform and stable mixture with scintillator easily because of the excellent solubility of supercritical carbon dioxide. So, in the $^{14}C$ testing device 1 which needs apply the scintillator, the sampling and preparation accuracy may be improved remarkably. Moreover, when the carbon dioxide is pretreated to supercritical state, it may be mixed with solid scintillator directly, and the adding of a certain amount of toluene PPO/POPOP scintillation solution is unnecessary to form the uniform and stable mixture.

Fourth Embodiment

Figure 7:
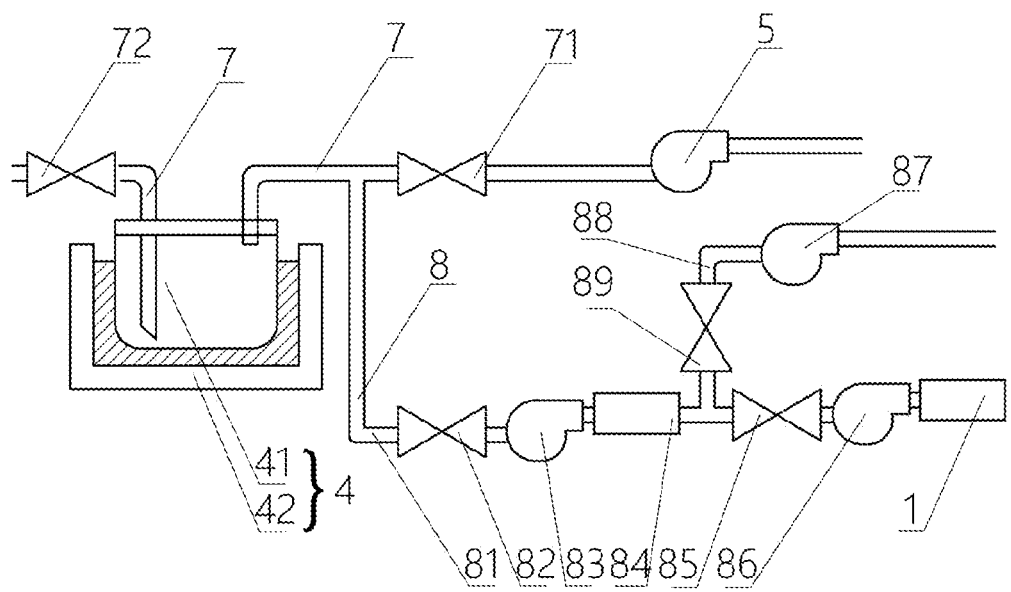
FIG. 7 is a connection diagram of the sampling and preparation system's carbon dioxide trap, carbon dioxide transferring device, pumping device and the $^{14}C$ testing device according to the fourth embodiment.

The fourth embodiment provides a sampling and preparation system, which further improves the sampling and preparation system in one of the first to third embodiments. The main improvement is that, in the fourth embodiment, as shown in the FIG. 7, the transferring device also includes the vacuum pump 87 connected with transferring pipeline 81 by the pipeline branch 88, and the vacuum valve 89 is positioned on the pipeline branch 88.

Figure 8:
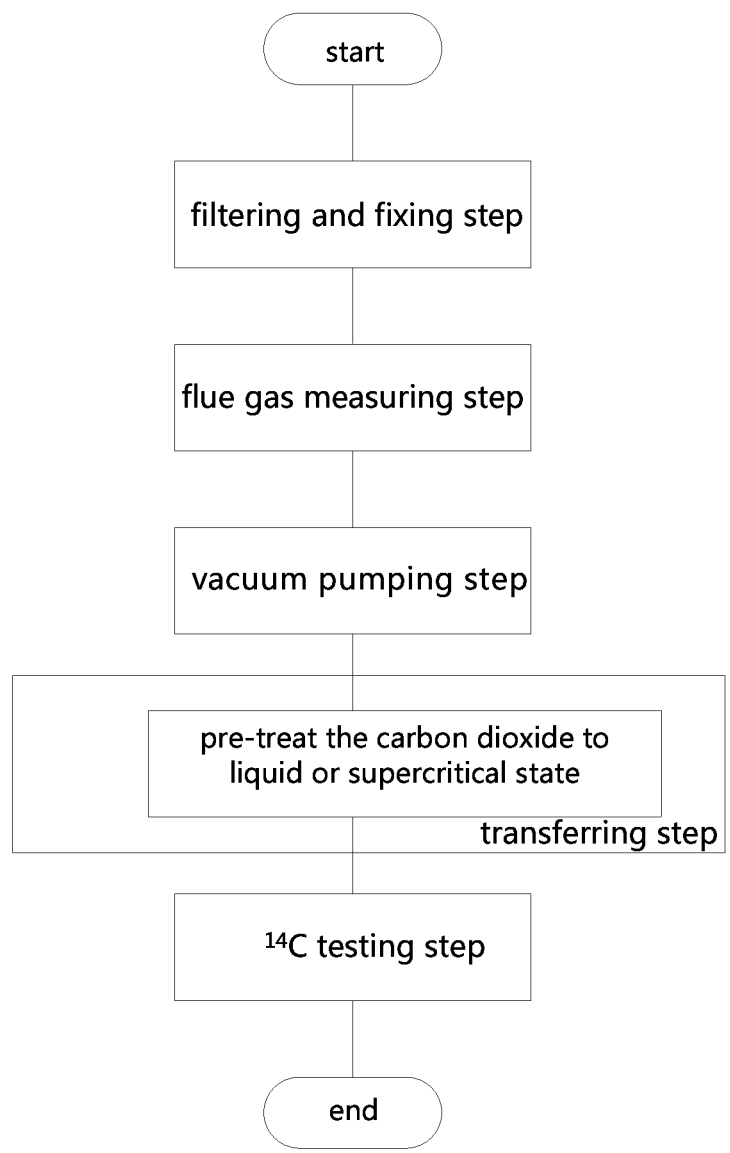
FIG. 8 is a flow chat of the sampling and preparation method according to the fourth embodiment.

The present embodiment also provides a kind of sampling and preparation method, which further improves the sampling and preparation system in one of the first to third embodiments. The main improvement is that, in the fourth embodiment, as shown in the FIG. 8, before the transferring step, it also includes the following step:

vacuum pumping step: Pumping the transferring device and the $^{14}C$ testing device 1 to vacuum.

The pipeline branch 88 may connect to any part of the transferring pipeline 81 between the first transferring valve 82 and the $^{14}C$ testing device 1.

Combining it with structure of the sampling and preparation system mentioned in the third embodiment specifically, the sampling and preparation process may include the following steps:

1. The first transferring valve 82 defaults is closed, while the prepositioned valve 72 and the evacuation valve 71 is open. The carbon dioxide passing though the carbon dioxide trap 4 is condensed constantly under the effect of a low temperature, and forms solid carbon dioxide in the capturing vessel 41.

2. Opening the vacuum valve 89 and pumping the transferring pipeline 81 to vacuum by using the vacuum pump 87. If the second transferring valve 85 exists, it is also possible to open the second transferring valve 85 to pump the $^{14}C$ testing device 1 to vacuum, so that the transferring device and the $^{14}C$ testing device 1 are all in negative pressure state. Generally, the vacuum degree is advised to be $10^{-1}$ Pa, or lower.

3. When enough carbon dioxide is captured in the carbon dioxide trap 4, closing the preposition valve 72, the evacuation valve 71 and the second transferring valve 85 (if it exists), and opening the first transferring valve 82 and the gas compressor 83. The solid carbon dioxide in the capturing vessel 41 is warmed slowly by the temperature adjusting device 42, and the carbon dioxide is sublimated to gas state. If the second transferring valve 85 exists, the carbon dioxide will occupy the negative pressure area rapidly except for the $^{14}C$ testing device 1. And if the second transferring valve 85 doesn't exist, the carbon dioxide will occupy all the negative pressure area.

4. The carbon dioxide gas is compressed under the action of the gas compressor 83. By controlling the pressure and temperature of the pressuring vessel 84, the liquid carbon dioxide or supercritical carbon dioxide is formed in the pressuring vessel 84. Specifically, when the carbon dioxide is required to form liquid state, the temperature of the carbon dioxide trap 4 may be warm to 0 degree Celsius to 10 degree Celsius slowly and the pressure in the pressuring vessel 84 may be controlled ranged from 2 MPa to 4 MPa. When the carbon dioxide is required to form supercritical state, the temperature of the carbon dioxide trap 4 may be warm to 30 degree Celsius to 40 degree Celsius slowly and the pressure in the pressuring vessel 84 may be controlled ranged from 7 MPa to 9 MPa.

5. After enough liquid or supercritical carbon dioxide has been gained, closing the first transferring valve 82, and opening the second transferring valve 85 and the transferring pump 86, the carbon dioxide is transferred into the $^{14}C$ testing device 1 by the transferring pump 86. Considering the carbon dioxide residue in the transferring pipeline 81, the content of the carbon dioxide stored in the pressuring vessel may be 1.2 to 2.0 times of one standard testing required, preferably 1.4 to 1.8 times.

Setting the vacuum pump 87 may pump the system to vacuum, which avoids the effect of original gas to the gas pressure, and improves the testing accuracy. The vacuum pump 87 also adapt to the structure of the second embodiment and other deformation structures.

Fifth Embodiment

Figure 9:
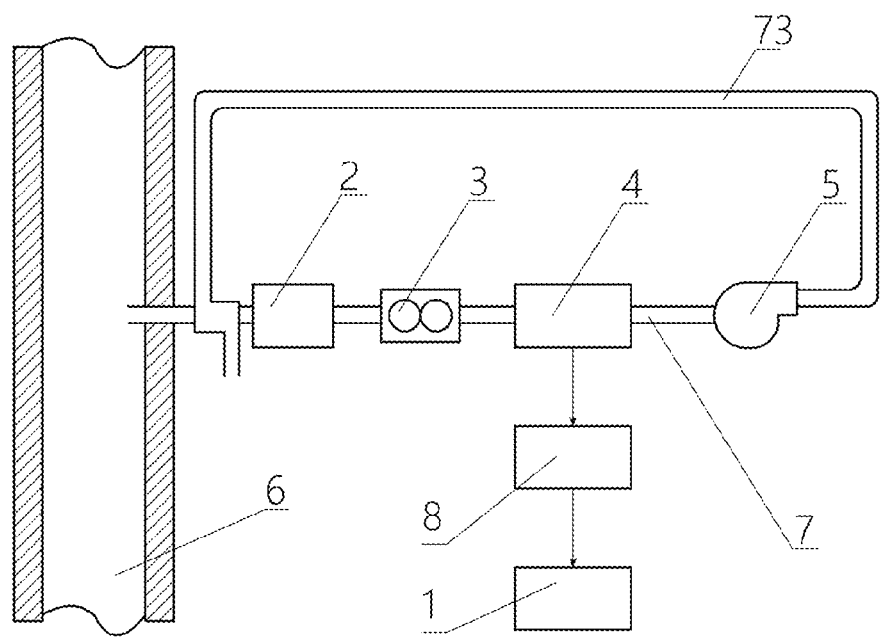
FIG. 9 is a connection diagram of the sampling and preparation system according to the fifth embodiment.

The fifth embodiment provides a sampling and preparation system, which further improves of the sampling and preparation system in one of the first to fourth embodiments. The main improvement is that, in the fifth embodiment, as shown in the FIG. 9, the sampling and preparation system also includes: The heat exchange pipeline 73 connected to the outlet of the pumping device 5. The heat exchange pipeline 73 is used to exchange the heat with the part on sampling pipe 7 between the boiler flue 6 and the filtering device 2.

Figure 10:
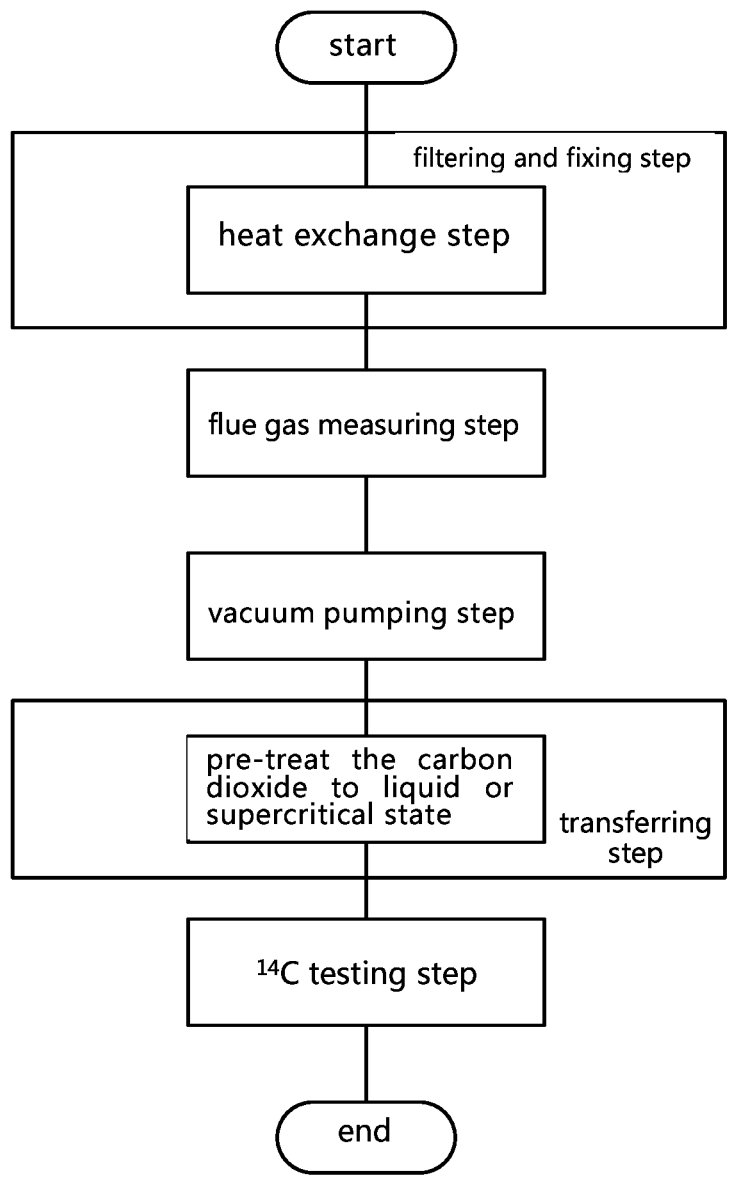
FIG. 10 is a flow chat of the sampling and preparation method according to the fifth embodiment.

The present embodiment also provides a kind of sampling and preparation method, which further improves the sampling and preparation method in one of the first to fourth embodiments. The main improvement is that, in the fifth embodiment, as shown in the FIG. 10, in the process of filtering and fixing step, it also includes the following sub-step.

Heat exchange step: non-contact heat transfer between the system exhaust gas and the flue gas entering the system is used to reduce the temperature of the flue gas entering the system.

Combining with the structure specifically, it happens during the sampling and preparation process.

In the flue gas entering the system, the carbon dioxide passing though the carbon dioxide trap 4 is condensed constantly under the effect of a low temperature, and forms solid carbon dioxide in the capturing vessel 41. However, the other low temperature exhaust gas is evacuated constantly by the action of the pumping device 5, which exchanges the heat with the front of the sampling pipe 7 through the heat exchange pipeline 73, so that the temperature of the flue gas entering the carbon dioxide trap 4 decreases dramatically. Because the heat exchange process is non-contact, the flue gas will not mix with the exhaust gas. Therefore, it may not only affect the measuring accuracy, but also save the energy consumption of the sampling and preparation system dramatically.

In summary, the heat exchange pipeline 73 may decrease the temperature of the flue gas entering the sampling and preparation system and decrease the cooling requirement of the carbon dioxide trap 4. It may save the system energy consumption, at the same time decrease the time required to fix carbon dioxide in the carbon dioxide trap 4 and improve the efficiency of sampling and preparation.

Sixth Embodiment

Figure 11:
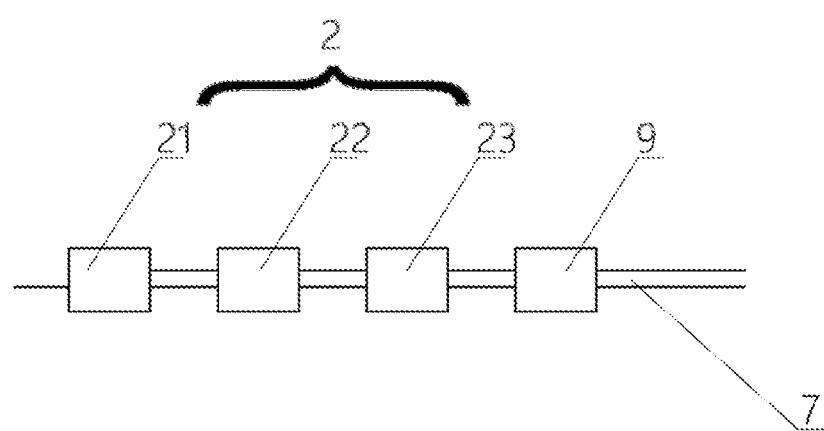
FIG. 11 is a schematic diagram of the sampling and preparation system's filtering device according to the sixth embodiment.

The sixth embodiment provides a sampling and preparation system, which further improves the sampling and preparation system in one of the first to fifth embodiments. The main improvement is that, in the sixth embodiment, as shown in the FIG. 11, the filtering devices 2 comprise the following sequentially connected units:

a preposition dust filter 21, a dryer 22, a postposition dust filter 23.

The flue gas suctioned by the sampling pump 7 is filtered primarily by passing the preposition filter 21. After removing the most particulate matter in the flue gas, the moisture and particulate matter in the flue gas is removed completely by passing the dryer 22 and the postposition filter 23 sequentially, which can ensure the normal operation of the mass flow controller 3.

Specifically, the postposition filter 23 may use HEPA rose box to enhance the filtering effect.

There is a cold trap 9 positioned between the mass flow controller 3 and the carbon dioxide trap 4, and the temperature of the cold trap 9 ranges from minus 40 degrees Celsius to minus 60 degrees Celsius.

The cold trap 9 may remove the impurity gases, the boiling point of which is higher than carbon dioxide, such as sulfur dioxide, nitrogen dioxide and sulfur anhydride and so on.

Figure 12:
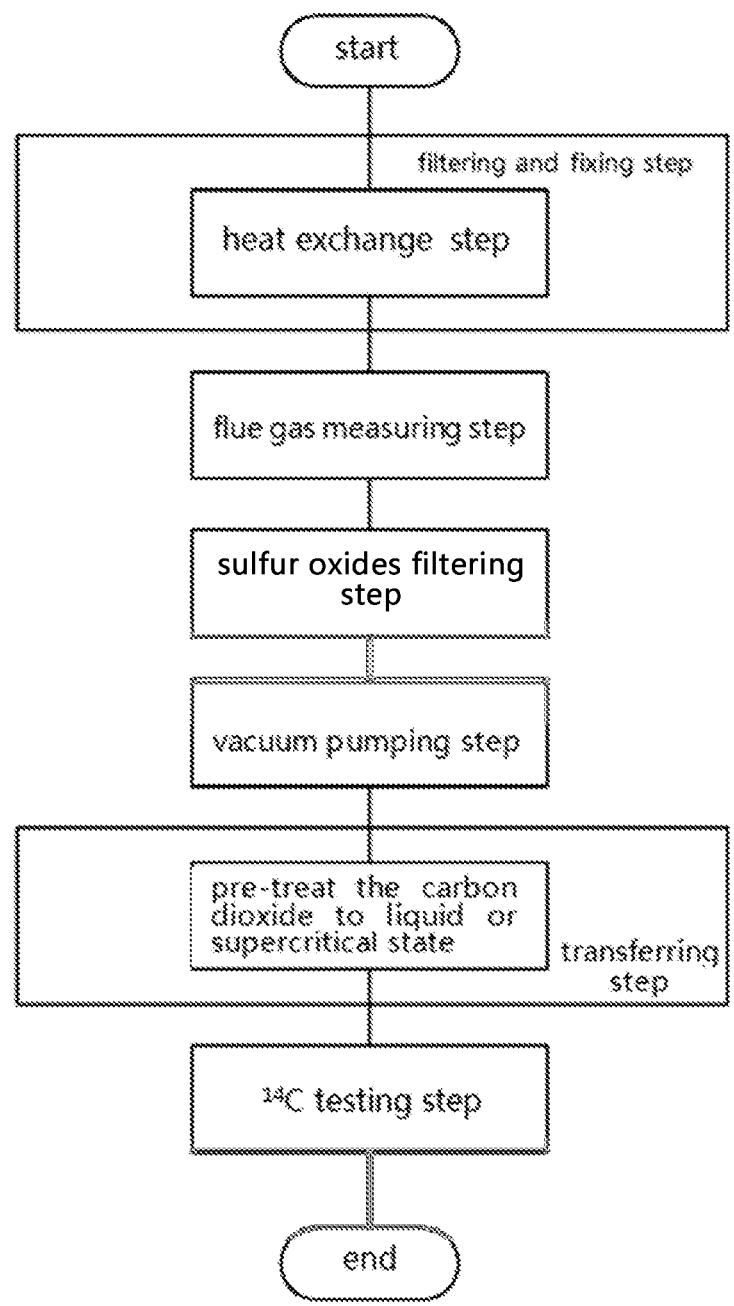
FIG. 12 is a flow chat of the sampling and preparation method according to the sixth embodiment.

The present embodiment provides a sampling and preparation system, which further improves the sampling and preparation system in one of the first to fifth embodiments. The main improvement is that, in the sixth embodiment, as shown in the FIG. 12, between the gas testing and transferring step, it also includes the following step.

Secondary filtering step: passing the flue gas through the cold trap 9 to remove the sulfur oxides and nitrogen oxides in the flue gas.

This embodiment improves the purity of carbon dioxide by using the filtering device 2 to filter the impurity in the flue gas and using the cold trap 9 to purify and fix carbon dioxide, then improves the detection accuracy. Liquid scintillation counter is used in this embodiment, and the cost of the instrument automation realizing may be reduced, which will improve the competition of the liquid scintillation counter in the application of biomass bending ratio detection.

Seventh Embodiment

The $^{14}C$ testing device 1 used in the embodiments of the present application may be a variety of $^{14}C$ testing device 1.

Especially, the scintillation counter 13 may be set, which used to measuring the $^{14}C$ in the carbon dioxide as the $^{14}C$ testing device 1.

Figure 13:
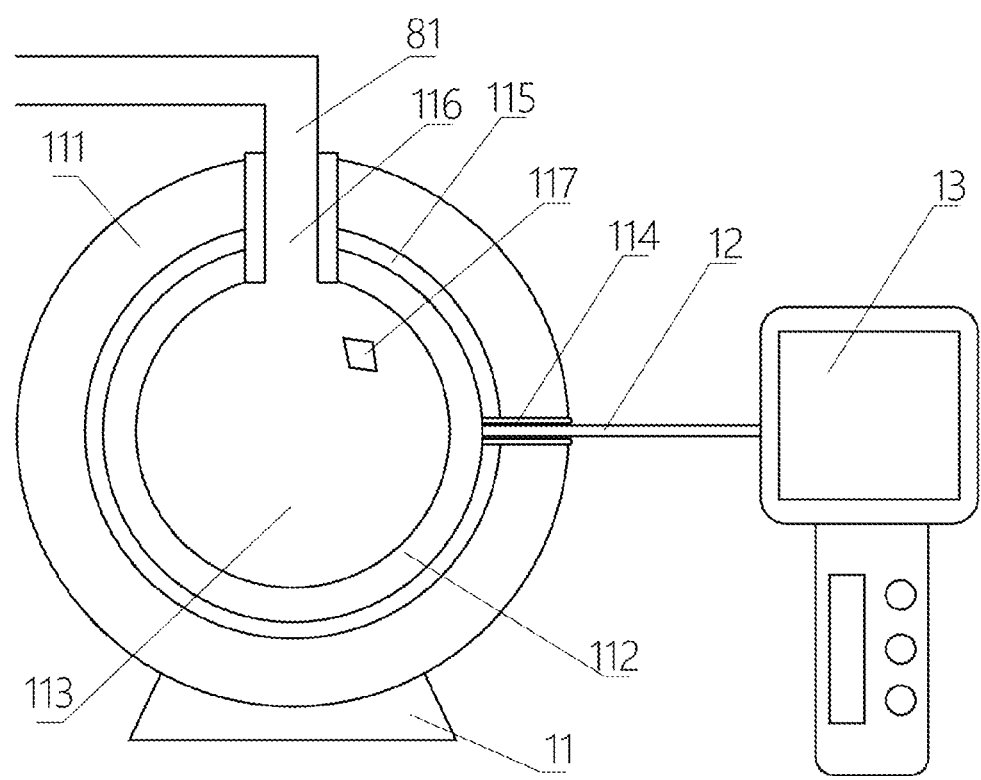
FIG. 13 is a schematic diagram of the sampling and preparation system's $^{14}C$ testing device according to the seventh embodiment.

Accordingly, the seventh embodiment provides a sampling and preparation system, which further improves the sampling and preparation system in one of the first to sixth embodiments. The main improvement is that, in the sixth embodiment, as shown in the FIG. 13, the $^{14}C$ testing device includes the optical fiber 12, the scintillation counter 13 and the $^{14}C$ testing bottle 11.

Specifically, the $^{14}C$ testing bottle 11 includes the pressure-bearing shell 111 and the sample bin 112 positioned in the pressure-bearing shell 111, and the cavity 113 which was connected with the injection port 116 on the $^{14}C$ testing bottle 11 is positioned in the sample bin 112. The injection port 116 connects with the transferring device.

Specifically, the sample bin 112 may diffuse the light produced in the cavity 113. At least part of the sample bin 112 is transparent, which is used to correspond to the optical fiber channel 114. There is an optical fiber channel 114 set on the pressure-bearing shell 111. One end of the optical fiber channel 114 is connected with the scintillation counter 13, and the other end of the optical fiber channel 114 is connected with the transparent part of the sample bin 112.

One end of the optical fiber 12 is inserted into the optical fiber channel 114, and the other end is connected to the scintillation counter 13.

In the present embodiment, the sample bin 112 may be most or all transparent, and the outer surface of the transparent part of the sample bin 112 is coated with a diffuse reflection coating.

In order to allow the photons to enter the optical fiber channel 114, reserving transparent part on the sample bin 112 is necessary. However, in order to allow most or all photons to enter the optical fiber channel 114, the diffuse reflection capacity of cavity 113 wall is necessary. Therefore, it is possible to make the sample bin 112 transparent and coat the transparent outer wall with a diffuse reflection coating, making it have enough diffuse reflection capacity. Specifically, the polyethylene(PE) may be used, and may be made thin shell with uniform wall thickness. The fully transparent sample bin 112 has the advantages of simple process and low cost. The titanium pigment may be chose as the coating material.

In the present embodiment, the insulation layer 115 is positioned between the pressure-bearing shell 111 and the simple bin 112. By setting the insulation layer 115, the storage time of carbon dioxide in the sample bin 112 may be prolonged.

Specifically, the insulation layer 115 may be foam material, plush material and so on.

When the insulation layer 115 is not set, the pressure-bearing shell 111 may provide the insulation function. However, the required temperature of carbon dioxide is low in the cavity 113, so the cost may be decreased dramatically by setting the insulation layer 115 which decreases the required thickness of the pressure-bearing shell 111. In addition, the insulation layer 115 may provide buffer for the sample bin 112 to prevent deformation.

As the common knowledge of this field, in the insulation layer 115, there should be holes corresponding to the optical fiber channel 114 to allow the pass of optical fiber 12.

As the further optimization of the present embodiment, it is possible to position the sensory assembly 117 in the cavity 113.

With the aid of the sensory assembly 117, the pressure in the cavity 113 may be adjusted more intuitively, and the phase state of the carbon dioxide may be conveniently adjusted.

In the present embodiment, it is possible to use wireless communication type sensory assembly 117 which is placed in the cavity 113 for each use. Of course, it is also possible to use the sensory assembly 117 with a wire rod, and the wire rod is embedded between the sampling bin 112 and the pressure-bearing shell 111. Using the wired connection may avoid the electromagnetic shielding to the wireless communication of sensory assembly 117 produced by the pressure-bearing shell 111, and also may ensure the power supply of the sensory assembly 117 better.

The sensory assembly 117 referred to in the present embodiment may be temperature sensor such as thermocouple, or pressure sensor. Specifically, the pressure sensor may embed to the inner wall of the simple bin 112 to improve the stability.

In the present embodiment, the cavity 113 is spherical or cylindrical. The spherical or cylindrical cavity 113 has better pressure-bearing capacity. The spherical cavity 113 may improve the uniformity of stress distribution in the cavity 113, and be convenient for the arrangement of optical fiber 12, reduce the geometric blind area and improve the counting efficiency of liquid scintillation counter. Of course, the other shape also may meet the requirement of the present invention basically.

Figure 14:
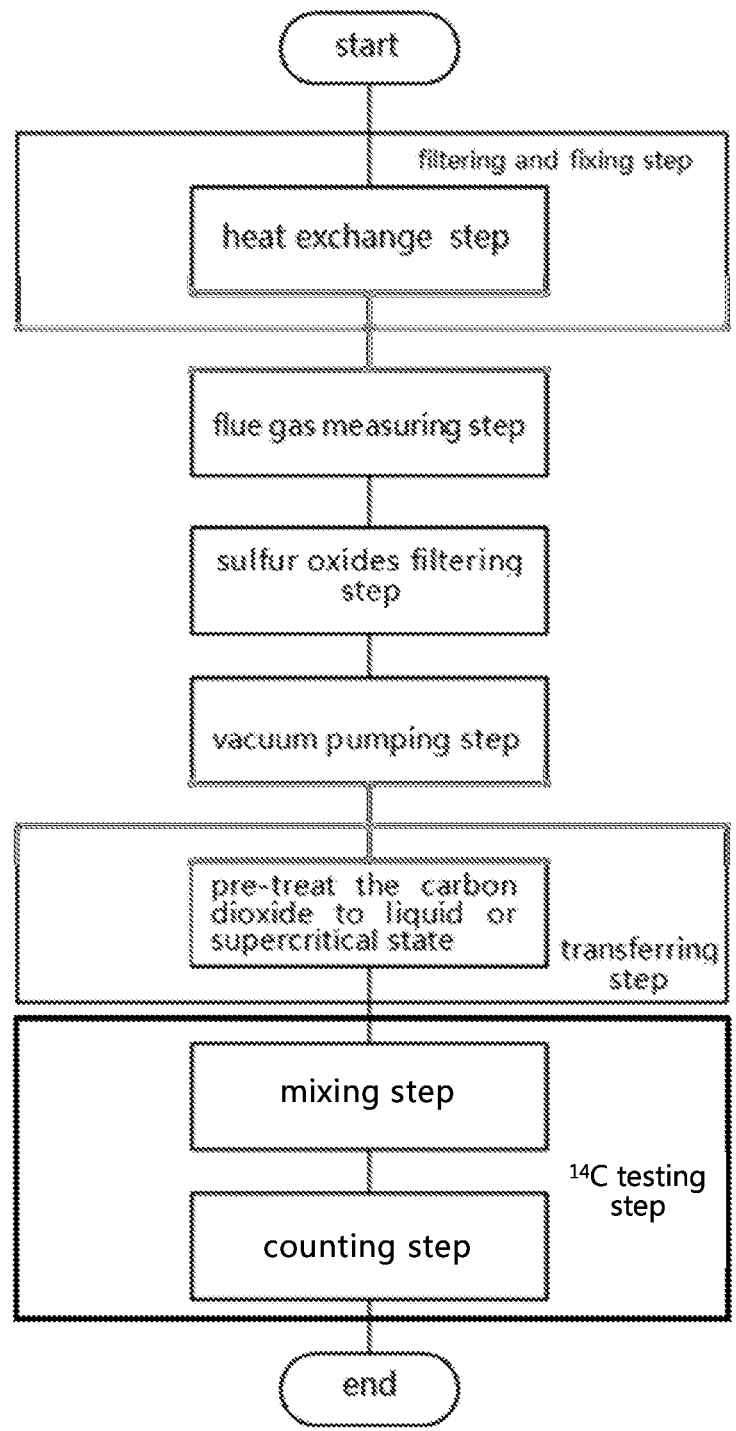
FIG. 14 is a flow chat of the sampling and preparation method according to the seventh embodiment.

The present embodiment also provides a sampling and preparation method which further improves the sampling and preparation method in one of the first to sixth embodiments. The main improvement is that, in the seventh embodiment, as shown in the FIG. 14, the mentioned $^{14}C$ measuring step includes the following sub-step:

mixing step: mixing up the liquid or supercritical carbon dioxide and scintillator in the $^{14}C$ testing bottle 11, then setting it in a dark condition for a preset standing time.

The standing time is 2 to 5 hours which may be increased or shorted according to the specific circumstances. Standing the sample in the dark for the preset time may eliminate the effect of chemiluminescence in the mixed liquor, and the preset time is not too long to induce the consumption of $^{14}C$.

Counting step: Inserting one end of the optical fiber 12 into the optical fiber channels 114 of the $^{14}C$ testing bottle 11, and the other end is connected to the scintillation counter 13, then start counting.

Specifically, during the mixing step, it is possible to pre-treat the carbon dioxide sample to liquid or supercritical state, or make the carbon dioxide the corresponding phase in the $^{14}C$ testing bottle 11 by controlling the environment temperature, in the process of injecting the carbon dioxide to $^{14}C$ testing bottle 11 through the pressure pipeline.

As optimization, the scintillator may be liquid (scintillation liquid) or solid (scintillation crystal).

Further, as optimization, when the carbon dioxide is liquid, certain PPO (2,5-two phenyl sulfamethoxazole) and POPOP (1,4-b is [2-(5-phenyl)] oxazolyl] benzene] may be dissolved in the toluene solution as a scintillation agent. Its specific formula may be PPO concentration of 30 g/L, POPOP concentration of 2 g/L toluene solution.

If the carbon dioxide is pretreated into liquid state, the mixing ratio of liquid carbon dioxide and scintillator is from 10:1 to 100:1 (volume ratio) during the mixing step.

If the carbon dioxide is pretreated into supercritical state, the mixing ratio of supercritical carbon dioxide and scintillator is from 0.16 L/g to 0.4 L/g (volume mass ratio).

If the scintillator is excessive, it may cause a decrease in the homogeneity and stability of the mixed liquor, thereby reducing the counting efficiency. However, if the scintillator is too little, it may make the dispersion density of the scintillator monomer in the mixed liquor is not high enough, and the produced photons will decrease because of less collision of the emitted beta electrons, thereby missing counting of the flashes, thus reducing the testing precision.

This mixing ratio may ensure the stability and homogeneity of the mixed liquor to be tested, and ensure the relatively high luminousefficiency of the scintillator, then improving the measurement accuracy.

In addition, when the carbon dioxide is in supercritical state, the 2-(4-Tert butyl phenyl)-5-(4-biphenyl)-1,3,4-oxdiazole(butyl-PBD) may be chosen as the scintillator.

By setting a pressure-bearing shell 111 outside the sample bin 112, the carbon dioxide in the cavity 113 of the sample bin 112 may be kept in a relatively stable phase state, so that the carbon dioxide may be fully mixed with the scintillator. By setting the cavity 113 which generates diffuse reflection, the high-energy electrons decay from the $^{14}C$ in the carbon dioxide may collide with the scintillator monomer, so that the scintillator monomer is in the excited state. When the scintillator monomer is de-excitation, a photon with a wavelength of about 380 nm will be generated. These photons may enter the external scintillation counter 13 through the optical fiber channel 114, so that the $^{14}C$ in the carbon dioxide sample may be measured. The $^{14}C$ testing bottle 11 has the advantages of simple structure, low cost, accurate test and short time needed. The $^{14}C$ testing method of the present invention mix liquid or supercritical carbon dioxide with the scintillator directly and stand it, compared with converting carbon dioxide into benzene, making chemical reactions of carbon dioxide unnecessary, which takes shorter testing time and more accurate measurement.

Eighth Embodiment

Figure 15:
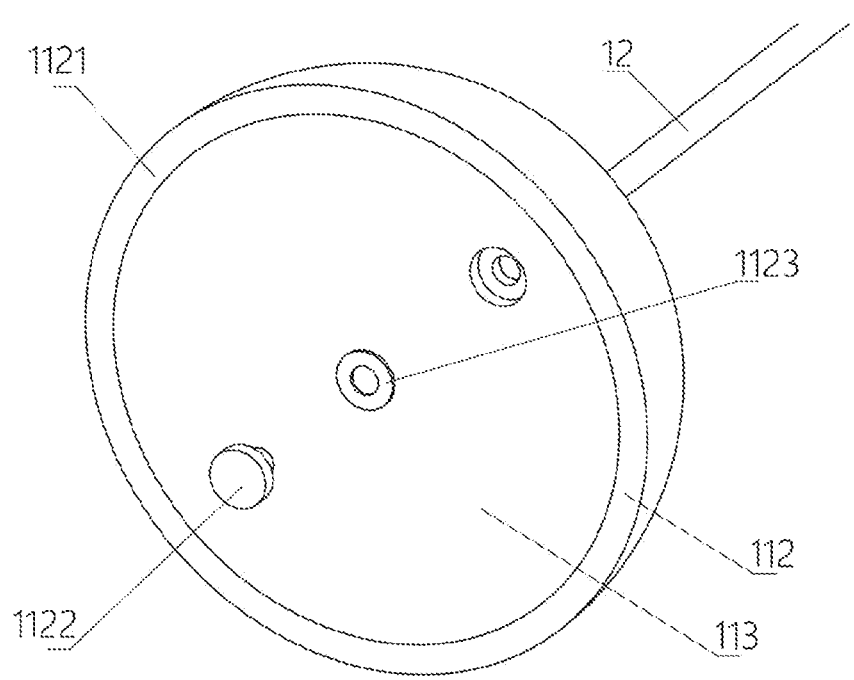
FIG. 15 is a 3D explosive schematic diagram of the joint between the optical fiber and the sample bin of the $^{14}C$ testing device according to the eighth embodiment.

The eighth embodiment provides a sampling and preparation system, which is different from the sampling and preparation system in the seventh embodiment. The main difference is that, in the seventh embodiment, the simple bin 112 is most or all transparent, but in the eighth embodiment, as shown in the FIG. 15, the simple bin 122 comprises the body 1121 and the transparent sheet 1122 embedded in the body 1121.

The body 1121 has the inner wall which diffuses the light generated in the body 1121. When the body 1121 of the sample bin 112 does not need to be made transparent, the materials for the sample bin 112 maybe more abundant, for example, the metal with strong compressive capacity, the ceramic with stronger reflection ability, the polymer material easy to manufacture and low-cost, etc. Furthermore, the body 1121 and the pressure-bearing shell 111 may be integral forming to reduce the process steps and equipment complexity.

As a typical optimization of the present embodiment, it is possible to make ladder-like hatches on the body 1121, and the corresponding transparent sheet 1122 is integral formed with the hatches. Thus, the transparent sheet 1122 may be pressed on the body 1121 to form a better seal by using the pressure in the cavity 113. Further, the sealing effect may be improved by setting seal ring 1123 in the between the transparent sheet 1122 and body 1121.

Ninth Embodiment

In the prior art, there is no automatic computing device for the calculation of biomass blending ratio. Accordingly, the ninth embodiment provides a computer storage media based on the sampling and preparation method in one of the first to seventh embodiments.

Specifically, the computer program is stored in the computer storage media. When the computer program is executed by the processor, the following steps are implemented.

The biomass blending ratio in the coal and biomass co-fired power station is calculated, according to the content of flue gas entering into the carbon dioxide trap 4 gained by the mass flow controller 3, and the $^{14}C$ measuring of the carbon dioxide entering into the carbon dioxide trap 4 detected by the $^{14}C$ testing device 1.

By the computer program, it is possible to calculate the biomass blending ratio automatically according to the gaining values.

Moreover, by using computer automatic processing, real-time biomass blending ratio curve may be provided for comparison and reference. Even when automated computing devices are connected to cloud communications, biomass blending ratio data may be provided to regulators in real time.

Setting up the biomass blending ratio monitoring equipment in coal and biomass co-fired power station may facilitate the government and institutions to supervise the power plant, and formulate more reasonable subsidy standards and policies.

Those of ordinary skill in the art can understand that many technical details are proposed to provide readers with a better understanding of the present invention. However, even if there are no technical details and variations and modifications based on the above embodiments, the technical solutions for the claims of the present application can be substantially realized. Therefore, in practice, various modifications can be made in form and detail to the above embodiments without departing from the spirit and scope of the present invention.

The invention claimed is:

1. A sampling and preparation system used for measuring a blending ratio of a coal and biomass co-fired power station, comprising:
    a sampling pipe connectable with a boiler flue of a co-fired power station, wherein the sampling pipe comprises the following elements sequentially arranged from an end close to the boiler flue to another end away from the boiler flue:
        a filtering device, a mass flow controller, a cold trap, a carbon dioxide trap and a pumping device, wherein the filtering device comprises the following sequentially connected units: a preposition dust filter, a dryer and a postposition dust filter, and wherein a temperature of the cold trap ranges from minus 40 degrees Celsius to minus 60 degrees Celsius;
    a carbon dioxide transferring device; and
    a $^{14}C$ testing device, the carbon dioxide transferring device being arranged to transfer carbon dioxide from the carbon dioxide trap into the $^{14}C$ testing device, and the $^{14}C$ testing device is configured to measure $^{14}C$ in the carbon dioxide.

2. The sampling and preparation system according to claim 1, wherein:
    the carbon dioxide trap comprises:
        a capturing vessel for fixing the carbon dioxide, and a temperature adjusting device for adjusting the temperature of the capturing vessel;

an evacuation valve positioned between the pumping device and the carbon dioxide trap on the sampling pipe;

a preposition valve is positioned between the mass flow controller and the carbon dioxide trap on the sampling pipe;

the transferring device comprises a transferring pipe line, one end of the transferring pipe line being connected with the carbon dioxide trap and another end of the transferring pipeline being connected with the $^{14}C$ testing device;

a first transferring valve positioned on the transferring pipeline.

3. The sampling and preparation system according to claim 2, wherein:

the transferring pipeline from the end close to the carbon dioxide trap to the end away from the carbon dioxide trap comprises the following sequentially arranged elements:

a gas compressor, a pressuring vessel, a second transferring valve and a transferring pump;

the first transferring valve is positioned between the gas compressor and the carbon dioxide trap;

the gas compressor is configured to compress the carbon dioxide to liquid or supercritical state in the pressuring vessel;

the transferring pump is configured to transfer the carbon dioxide from the pressuring vessel into the $^{14}C$ testing device.

4. The sampling and preparation system according to the claim 2, wherein:

the transferring device further comprises a vacuum pump, which is connected with the transferring pipeline by a pipeline branch, and a vacuum valve is positioned on the pipeline branch;

the sampling and preparation system further comprises: a heat exchange pipeline connected to an outlet of the pumping device;

the heat exchange pipeline is configured to exchange the heat with a part on sampling pipe between the boiler flue and the filtering device.

5. The sampling and preparation system according to claim 1, wherein:

the $^{14}C$ testing device comprises an optical fiber, a scintillation counter and a $^{14}C$ testing bottle;

the $^{14}C$ testing bottle comprises a pressure-bearing shell and a sample bin positioned in the pressure-bearing shell, a cavity is arranged in the sample bin and the $^{14}C$ testing bottle is provided with an injection port connected to the cavity; the injection port is connected with the transferring device;

the sample bin is configured to diffuse light produced in the cavity;

a scintillator is preset in the cavity;

at least part of the sample bin is transparent, an optical fiber channel is set on the pressure-bearing shell, wherein one end of the optical fiber channel is connected with the scintillation counter and another end of the optical fiber channel is connected with the transparent part of the sample bin;

an insulation layer is positioned between the pressure-bearing shell and the simple bin;

a sensory assembly is positioned in the cavity and the sensory assembly is a pressure sensor and/or a temperature sensor;

the cavity is spherical or cylindrical;

one end of the optical fiber is inserted into the optical fiber channel of the $^{14}C$ testing bottle, and another end of the optical fiber is connected to the scintillation counter.

6. A sampling and preparation method used for measuring $^{14}C$ in a boiler flue of a coal and biomass co-fired power station, comprising the following acts:

filtering and fixing step: filtering particulate matter and water in flue gas from the boiler flue, and fixing carbon dioxide of the filtered flue gas in a carbon dioxide trap;

flue gas measuring step: obtaining an amount of the filtered flue gas entering the carbon dioxide trap by a mass flow controller;

transferring step: transferring the carbon dioxide from the carbon dioxide trap into the $^{14}C$ testing device, comprising the following sub-act:

pretreating the carbon dioxide to a liquid or supercritical state; and $^{14}C$ testing step: measuring the $^{14}C$ of the carbon dioxide in the $^{14}C$ testing device.

7. The sampling and preparation method according to claim 6, further comprising the following act between the gas testing act and the transferring act:

secondary filtering step: passing the flue gas through a cold trap to remove sulfur oxides and nitrogen oxides in the flue gas.

8. The sampling and preparation method according to claim 6, comprising the following sub-act in the $^{14}C$ testing step:

mixing step: mixing up the liquid carbon dioxide or supercritical carbon dioxide and a scintillator to produce a mixture, then setting the mixture in a dark condition for a preset standing time;

counting step: counting the mixture by using a scintillation counter;

if the carbon dioxide is pretreated into the liquid state, a mixing ratio of the liquid carbon dioxide and the scintillator is from 10:1 to 100:1 (volume ratio) during the mixing step;

if the carbon dioxide is pretreated into the supercritical state, a mixing ratio of the supercritical carbon dioxide and the scintillator is from 0.16 L/g to 0.4 L/g (volume mass ratio).

9. A sampling and preparation system used for measuring a blending ratio of a coal and biomass co-fired power station, comprising:

a sampling pipe connectable with a boiler flue of a co-fired power station, wherein the sampling pipe comprises the following elements sequentially arranged from an end close to the boiler flue to another end away from the boiler flue:

a filtering device, a mass flow controller, a carbon dioxide trap and a pumping device;

a carbon dioxide transferring device; and a $^{14}C$ testing device, the carbon dioxide transferring device being arranged to transfer carbon dioxide from the carbon dioxide trap into the $^{14}C$ testing device, and the $^{14}C$ testing device is configured to measure $^{14}C$ in the carbon dioxide, wherein:

the $^{14}C$ testing device comprises an optical fiber, a scintillation counter and a $^{14}C$ testing bottle;

the $^{14}C$ testing bottle comprises a pressure-bearing shell and a sample bin positioned in the pressure-bearing shell, a cavity is arranged in the sample bin and the $^{14}$C testing bottle is provided with an injection port connected to the cavity; the injection port is connected with the transferring device;

the sample bin is configured to diffuse light produced in the cavity;

a scintillator is preset in the cavity;

at least part of the sample bin is transparent, an optical fiber channel is set on the pressure-bearing shell, wherein one end of the optical fiber channel is connected with the scintillation counter and another end of the optical fiber channel is connected with the transparent part of the sample bin;

an insulation layer is positioned between the pressure-bearing shell and the simple bin;

a sensory assembly is positioned in the cavity and the sensory assembly is a pressure sensor and/or a temperature sensor;

the cavity is spherical or cylindrical;

one end of the optical fiber is inserted into the optical fiber channel of the $^{14}$C testing bottle, and another end of the optical fiber is connected to the scintillation counter.

\* \* \* \* \*